(12) United States Patent
Muller (10) Patent No.: US 11,115,643 B2
(45) Date of Patent: Sep. 7, 2021

(54) ALIGNMENT SYSTEM

(71) Applicant: XION GMBH, Berlin (DE)

(72) Inventor: Holger Muller, Glienicke-Nordbahn (DE)

(73) Assignee: XION GMBH

( * ) Notice: Subject to any disclaimer, the term of this patent is extended or adjusted under 35 U.S.C. 154(b) by 358 days.

(21) Appl. No.: 15/700,451

(22) Filed: Sep. 11, 2017

(65) Prior Publication Data

US 2018/0084239 A1 Mar. 22, 2018

(30) Foreign Application Priority Data

Sep. 16, 2016 (DE) .......................... 102016217792.3

(51) Int. Cl.
*H04N 13/246* (2018.01)
*G06T 7/80* (2017.01)
(Continued)

(52) U.S. Cl.
CPC ....... *H04N 13/246* (2018.05); *A61B 1/00057* (2013.01); *A61B 1/00193* (2013.01);
(Continued)

(58) Field of Classification Search
CPC ................. H04N 13/246; H04N 5/232; H04N 2005/2255; H04N 13/189; H04N 5/23229;
(Continued)

(56) References Cited

U.S. PATENT DOCUMENTS 8,223,193 B2 7/2012 Zhao et al.
9,299,153 B2 3/2016 Aoki
(Continued)

FOREIGN PATENT DOCUMENTS

| DE | 19536297 A1 | 4/1997 |
|---|---|---|
| JP | 2009-258427 A | 11/2009 |
| WO | 2015/000056 A1 | 1/2015 |

OTHER PUBLICATIONS

German Search Report dated May 24, 2017 from corresponding Application No. DE 10 2016 217 792.3, 8 pages.
(Continued)

*Primary Examiner* — Joseph Suh
(74) *Attorney, Agent, or Firm* — Ware, Fressola, Maguire & Barber LLP (57) ABSTRACT

A method for adjusting an optical system, and to an adjustment system for use in an optical system where the adjustment system comprises a predetermined reference object having known visible reference object features, a sensor system, a data evaluation module and an image processor. The data evaluation module receives captured image data and determines at least two visible reference object features of the predetermined reference object arranged in a field of view, and determines position data containing a position deviation of an image of the object to be examined or, in the case of a stereoscopic optical system, of a first and second half-image of the object to be examined. The image processor ascertains an optical distortion of the visible reference object features and sets a corresponding geometric rectification of received image data.

17 Claims, 6 Drawing Sheets

(51) Int. Cl.
*H04N 13/189* (2018.01)
*A61B 1/00* (2006.01)
*G02B 30/35* (2020.01)
*G02B 7/00* (2021.01)
*H04N 5/232* (2006.01)

(52) U.S. Cl.
CPC .............. *G02B 7/003* (2013.01); *G02B 30/35* (2020.01); *G06T 7/85* (2017.01); *H04N 5/23229* (2013.01); *H04N 13/189* (2018.05); *G06T 2207/10068* (2013.01)

(58) Field of Classification Search
CPC ............. G06T 7/85; G06T 2207/10068; A61B 1/00057; A61B 34/20; A61B 1/00009; A61B 1/00163; A61B 1/045; A61B 7/85; A61B 1/00193; G02B 23/24; G02B 27/22; G02B 27/62; G02B 7/003; G02B 27/2235; G03B 35/10
See application file for complete search history.

(56) References Cited

U.S. PATENT DOCUMENTS

| | | | |
|---|---|---|---|
| 9,319,666 B1 | 4/2016 | Lisin | |
| 2003/0156525 A1* | 8/2003 | Fan | G11B 7/24 369/110.04 |
| 2005/0170808 A1 | 5/2005 | Evans et al. | |
| 2011/0115882 A1* | 5/2011 | Shahinian | A61B 1/05 348/45 |
| 2012/0290134 A1* | 11/2012 | Zhao | B25J 9/1689 700/259 |
| 2013/0085329 A1* | 4/2013 | Morrissette | A61B 1/00193 600/111 |
| 2013/0242052 A1* | 9/2013 | Hayashi | A61B 1/00193 348/45 |
| 2013/0258044 A1* | 10/2013 | Betts-Lacroix | H04N 5/2258 348/36 |
| 2014/0184814 A1* | 7/2014 | Lin | G06T 7/80 348/187 |
| 2014/0300754 A1* | 10/2014 | Hsieh | H04N 17/002 348/187 |
| 2015/0304617 A1* | 10/2015 | Chang | H04N 13/254 348/189 |
| 2015/0317821 A1* | 11/2015 | Ding | G06T 15/10 345/420 |
| 2016/0150211 A1* | 5/2016 | Hwang | H04N 13/133 348/43 |
| 2017/0336284 A1* | 11/2017 | Goldberg | G01M 11/0242 |
| 2018/0073857 A1* | 3/2018 | Cao | H04N 13/243 |
| 2018/0173965 A1* | 6/2018 | Pan | G08B 25/08 |
| 2019/0246017 A1* | 8/2019 | Tsuchida | H04N 5/2254 |

OTHER PUBLICATIONS

European Search Report dated Feb. 5, 2018 from corresponding Application No. EP 17190919.5, 9 pages.
Chinese Office Action dated Jan. 15, 2021 from corresponding Application No. 201710839547.4, 11 pages.
Stehle, Thomas et al.: "Dynamic Distortion Correction for Endoscopy Systems with Exchangeable Optics", Image Processing for Medicine, Jan. 1, 2009, Springer, Berlin, pp. 142-146.
Wengert, Christian et al: "Fully Automatic Endoscope Calibration for Intraoperative Use", Image Processing for Medicine, Jan. 1, 2006, Springer, pp. 419-423.
Schwalbe, Marius et al: "Design and Implementation of a Laparoscope Calibration Method for Augmented Reality Navigation", Provisions of the 14th Anniversary of the German Society for Computer and Robot-Assisted Surgery E.V, Sep. 1, 2015, 6 pages.
Melo, Rui et al.: "A New Solution for Camera Calibration and Real-Time Image Distortion Correction in Medical Endoscopy Initial Technical Evaluation", IEEE Transactions on Biomedical Engineering, IEEE Service Center, Piscataway, NJ USA, Mar. 1, 2012, pp. 634-644.

* cited by examiner

ALIGNMENT SYSTEM

CROSS REFERENCE TO RELATED APPLICATION

This application claims priority under 35 USC § 119 to German Patent Application No. 10 2016 217 792.3 filed on Sep. 16, 2016, which application is hereby incorporated by reference in its entirety.

TECHNICAL FIELD

The invention relates to a method for adjusting a stereoscopic optical system. Furthermore, the invention relates to an adjustment system for use in a stereoscopic optical system, the use of an adjustment system, a medical stereoscopic apparatus, in particular a stereo endoscope and a rigid endoscope for application with navigation systems, and a computer program.

BACKGROUND OF THE INVENTION

In optical apparatuses such as, for example, rigid endoscopes and also other medical optical apparatuses featuring optical image transmission, significant deviations of the image position from the ideal of a completely centered optical system can occur. They are caused by manufacturing tolerances, thermal expansion or a mechanical flexure of the optical apparatus. In this regard, a flexure in the case of such image-transmitting optical systems can lead to significant alterations of an image that is output, owing to the high number of optical elements present in endoscopes, for example.

A relative adjustment of the stereoscopic half-images is particularly important in stereoscopy. Otherwise, the stereoscopic image impression is impaired and fatigue of the observer occurs.

U.S. Pat. No. 8,223,193 B2 describes a calibration assembly comprising an interface for fixed arrangement on an endoscopic imaging system, a target object connected to the interface in the field of view of the imaging system, and a processor. The processor is configured to identify markings on first and second images from a first and second arrangement of imaging system and target object with respect to one another. In this case, the arrangement and the identified markings are used to determine calibration data for the endoscopic imaging system.

SUMMARY OF THE INVENTION

The aim of the invention is to provide an improved method for adjusting a stereoscopic optical system.

According to the invention, this aim is achieved in the case of a first aspect of the invention by means of a method for adjusting an optical system, in particular a stereoscopic optical system. The method comprises first, static adjustment steps and second, dynamic adjustment steps. The first, static adjustment steps comprise the following steps:

arranging a predetermined reference object having known visible reference object features in a field of view captured by the optical system;

capturing an image—provided by the optical system—of the predetermined reference object or, in the case of a stereoscopic optical system, a first and/or second half-image of the predetermined reference object by means of a sensor system, in particular in the form of reference object data;

determining position information of at least two visible reference object features of the predetermined reference object that are imaged in the image or in the first and/or second half-images;

ascertaining an optical distortion of the image or of the first and/or second half-image from the position information of the at least two visible reference object features;

adjusting an image processor, which is at least indirectly connected to the sensor system, by setting a geometric rectification in a manner corresponding to the optical distortion ascertained.

Furthermore, the method comprises the following second, dynamic adjustment steps during operation of the optical system for capturing an object to be examined:

arranging the object to be examined in the field of view captured by the optical system;

capturing position data containing a position deviation—determined by means of at least one reference point—of an image—provided by the optical system—of the object to be examined or, in the case of a stereoscopic optical system, of a first and second half-image of the object to be examined by means of the sensor system; and adjusting the image processor in a manner corresponding to the captured position deviation by setting a corresponding displacement of the image or of the first and second half-image relative to one another by means of the image processor.

Firstly, therefore, an optical distortion is ascertained and an image processor is adjusted such that it compensates for the ascertained optical distortion by geometric rectification. This step can be carried out statically with the aid of a reference object and need not be continually repeated, since the optical distortion of the optical system typically does not change during operation.

Subsequently, a position deviation can be captured and the image processor can be adjusted such that it compensates for the position deviation ascertained by displacing the image or the first and second half-images. This compensation of the position deviation can be carried out repeatedly—that is to say dynamically—during regular operation in order to compensate ad hoc for position deviations that occur during operation.

One aspect, therefore, is the division of the method into static and dynamic adjustment steps.

One aspect to be realized also independently thereof is the aspect that firstly the optical distortion is compensated for, and afterward a possible position deviation.

Particular advantages are afforded if both aspects as outlined above are combined, specifically in particular when adjusting a stereoscopic optical system, because the compensation of the position deviation of the half-images is of particular relevance in that case in order to avoid double images.

An improved adjustment and a distortion correction of the optical system are advantageously achieved by means of the method according to the invention. In this case, the image or, in the case of a stereoscopic optical system, the two stereoscopic half-images is or are rectified and displaced in a manner corresponding to a position deviation. In particular, both a distortion correction and a correction between the mutual position of the first and second half-images among one another are performed in the particularly advantageous stereoscopic case. Distortion here is understood to mean the dependence of the imaging scale of an imaging channel of the optical system on an image location and in particular on a field angle.

The number of reference object features used for adjustment must be at least two. This can involve for example the curvature and position of a straight line on a measurement chart. A larger number of reference object features can be chosen in order to increase an adjustment accuracy.

It is advantageous that the method comprises both static adjustment steps, which are carried out with the reference object, and dynamic adjustment steps during the operation of the optical system for capturing an object to be examined. Correction during operation, that is to say during a surgical operation, for example, is made possible as a result. Moreover, the correction is accelerated during operation since the distortion corrected during the static adjustment steps need no longer be corrected dynamically, as a result of which the processing time of the dynamic adjustment steps is reduced. By virtue of the fact that parameters have to be determined very little during the dynamic adjustment steps, the method according to the invention can increase the reliability and accuracy of the image processing at low data rates. In particular, a high accuracy of the adjustment can be achieved even with a small number of image field points to be measured of the object to be examined.

The static adjustment steps have to be performed significantly less frequently than the dynamic adjustment steps, without a quality of the adjustment of the optical system being significantly impaired as a result. Therefore, the system according to the invention also leads to a short overall adjustment duration and correspondingly to a low outlay for the adjustment.

It is furthermore advantageous that the method can be carried out largely in an automated manner such that it can be performed rapidly, safely and in an uncomplicated manner by users of the optical system, that is to say for example medical technical personnel, even without special knowledge in the field of camera adjustment or calibration.

Since the method is restricted to steps of image processing, it can be used for many stereoscopic optical systems. Consequently, it has many possible stereoscopic fields of application not restricted to the application for stereo endoscopes that is emphasized hereinafter.

Field of view is understood hereinafter to mean the space in which objects can be captured by the optical system and pass into an eye or onto an image sensor for imaging purposes.

A geometric rectification is set by means of an electronic or optical alteration of a geometric position of pixels with respect to one another in a manner corresponding to the optical distortion ascertained.

In the context of the invention, a reference object can be any object having known visible reference object features. In particular, a printed sheet with marking, a printed film, a structured background or a geometric body arranged in a predetermined manner can advantageously be used as a reference object.

Preferred embodiments of the method according to the invention are mentioned below.

In one preferred embodiment, the at least one reference point from which the position data are determined is a pixel of the image or of the first and/or second half-image. In other embodiments, the at least one reference point is a geometric distance indication or a mechanical pressure, which are determined by mechanical deformation sensors of the optical system and which imply the presence of a deformation of the optical system and also a measure of the deformation.

In one variant, the optical system uses for this purpose an optical reference beam that passes within the beam path of the optical system and in this case does not leave the optical system in the direction of the object to be examined. In the variant, this is realized for example by means of a mirror on an object side—facing the object—of the optical system, which mirror is at least partly reflective for the optical reference beam at least in one wavelength range.

In one preferred embodiment, the position data describe a geometric distance. In a further embodiment, the position data describe acceleration information, wherein a position in this case is determined from position data of the at least one reference point at at least two different points in time. This is particularly advantageous for the adjustment of the image processor given the presence of a regular movement of the optical system and/or of the object to be examined, such as, for example, in the case of wobbling of the optical system. In this case, the image processor can be adjusted particularly accurately since position data at a different point in time are also taken into account for the adjustment.

In a further embodiment, the position data are captured via a navigation system. In this case, the navigation system is configured to monitor a position and/or alignment of a distal part of the optical system, said distal part facing the object. The construction and functioning of such navigation systems are already generally known in particular for applications in the medical field and here in particular for applications in the field of endoscopy.

The capture of the position deviation is realized by the following sequence in one embodiment for a stereoscopic endoscopic system:
 arranging the object to be examined and having a predetermined visible examination object feature in the field of view captured by the optical system;
 capturing a first and second half-image—provided by the optical system—of the object to be examined by means of the sensor system, in particular capturing examination object data;
 determining a first vertical and/or horizontal image coordinate of the examination object feature in the first half-image and a second correspondingly vertical and/or horizontal image coordinate of the examination object feature in the second half-image,
  wherein a possible horizontal image coordinate is determined with respect to a horizontal image axis which lies within an image plane of the stereoscopic optical system and intersects both optical axes of the stereoscopic optical system, and
  wherein a possible vertical image coordinate is determined with respect to a vertical image axis which lies within the image plane of the optical system and perpendicularly to the horizontal image axis.

In the context of the invention, the respective vertical or horizontal image coordinates can be determined along the vertical or horizontal image axis, but also along a direction which is oriented substantially along the vertical or horizontal image axis, but does not correspond thereto.

Furthermore, the vertical or horizontal image coordinates can be obtained as virtual image coordinates directly from an imaging of the object to be examined or by processing of the examination object data.

The use of vertical image coordinates is particularly advantageous. In many applications of stereoscopic optical systems, a distance between object to be examined and optical system is not known, such that an offset between horizontal coordinates of an examination object feature on account of parallax is desired and accordingly should not be corrected. By contrast, an offset of the vertical image coordinates constitutes an undesired error in most possible applications of stereoscopic optical systems. Therefore, in preferred embodiments of the method according to the invention, at least the vertical image coordinates of the examination object feature are used for setting a corresponding displacement of the first and second half-images.

In one embodiment, the method also comprises projecting measurement marks onto the object to be examined and/or the image or, in the case of a stereoscopic optical system, onto at least one of the half-images.

In a further embodiment, the sensor system is equipped with sensors for capturing the decentration of the optical system and/or the position and orientation of the optical system and/or of the at least one object arranged in the field of view. By this means, in accordance with the method according to the invention, the position data for the adjustment are captured by the image processor.

In one embodiment, setting the corresponding displacement is carried out in such a way that image information processed by the geometric rectification is displaced in a manner corresponding to the position data.

In an alternative embodiment with respect thereto, setting the corresponding displacement is carried out in such a way that image information displaced in a manner corresponding to position data is processed by the geometric rectification. In one preferred variant of the two previous embodiments, it is possible to choose between the two embodiments. As a result, a user of the optical system can choose an order of displacement and rectification that is particularly suitable for the object to be examined or the substantive situation present. In one particularly preferred embodiment variant, the optical system is stereoscopic, and the image information is displaced in a manner corresponding to the vertical and/or horizontal image coordinates.

In a further embodiment, a stereoscopic optical system is present and a difference in the vertical image coordinates for the adjustment is provided to the image processor. In this case, an estimation of an actual displacement can be determined under the assumption that both half-images are misadjusted to identical extents.

In a further embodiment, the setting of the geometric rectification and/or the setting of the displacement are/is stored as adjustment parameter(s). As a result, it is advantageously possible to have recourse to the corresponding adjustment parameters at a later point in time. This allows a low data rate for carrying out the method according to the invention for adjustment, and therefore also a short method duration. The variant of this embodiment in which at least the setting of the geometric rectification is stored is particularly advantageous, since as a result this method step need only be performed infrequently. This exploits the circumstance that the geometric rectification need not be carried out before every capture of the object to be examined if corresponding adjustment parameters that have already been stored are present and can be used. In one variant, the setting of the geometric rectification, that is to say of the static adjustment steps, is carried out only once after the production of the corresponding optical system. In this case, the associated adjustment parameters are stored and only the dynamic adjustment steps are performed by the user of the optical system.

In one embodiment for a stereoscopic optical system, the first and second half-images of the predetermined reference object are captured by the sensor system, and adjusting the image processor is carried out by a comparison of the at least two known visible reference object features imaged on the first half-image with the at least two known visible reference object features imaged on the second half-image. As a result, the optical distortion can be determined particularly accurately, as a result of which a very accurate geometric rectification can be set. In one preferred variant, more than two, preferably more than eight, known visible reference object features on the first and second half-images are compared with one another.

In a further variant of the previous embodiment, the method comprises, besides ascertaining the optical distortion, ascertaining a difference in magnification between the first and second half-images, or a relative displacement between the first and second half-images, or a rotation between the first and second half-images, or a combination thereof. In one preferred example of this variant, all correspondingly ascertained adjustment parameters are used in order to set a uniform magnification of the first and second half-images, a compensation with respect to the relative displacement between the first and second half-images, or a compensation with respect to the rotation between the first and second half-images, or a combination thereof. The quality of the adjustment carried out in accordance with the method can be improved further as a result. In this case, ascertaining the relative displacement can be realized by determining vertical and horizontal image coordinates of the known visible reference object features such as during operation of the optical system.

As a result, a static precorrection of the first and second half-images is advantageously provided, such that only small displacements of the first and second half-images relative to one another have to be carried out by the image processor during the operation of the optical apparatus. The method duration during operation for capturing an object to be examined can be significantly reduced as a result.

In an alternative embodiment, only the first half-image is captured by the sensor system and used for the determination of the position information of the at least two visible reference object features. The method duration for the static method steps carried out by means of a reference object can be reduced as a result. In one variant of this embodiment, the first half-image is used for the geometric rectification of both half-images.

In a further embodiment, the at least one reference point is formed by providing a light beam directed onto the object to be examined. As a result, the method is applicable to a particularly large variety of objects to be examined, since the object need not have dedicated examination object features that serve as reference points. Furthermore, in accordance with this embodiment, complex steps of adaptation for example of the sensor system to predetermined visible reference points are not necessary, or necessary only once. The use of a light beam also advantageously has the effect that it is not necessary to attach a marking as examination object feature on the object to be examined if the object has no suitable examination object features. In one variant of this embodiment, the light beam is provided in a predetermined spectral range, such that the sensor system can receive a corresponding image of the light beam and the light beam is not perceived by the user of the optical system. In another variant of this embodiment, the light beam is provided in a pulsed manner, such that the light beam is not perceived by the user of the optical system for a large part of an examination duration. As a result, the capture of the object to be examined by the optical system is adversely affected to a particularly small extent, or not at all. In one variant, the light beam forms a structured illumination of the object. A structured illumination is understood to mean an illumination with a predetermined and non-homogeneous intensity distribution of an intensity of the light beams on the object to be illuminated or in the field of view to be illuminated. As a result, a multiplicity of reference points can be provided in a particularly simple manner.

In order to achieve the object mentioned above, an adjustment system for use in an optical system, in particular in a stereoscopic optical system, for capturing an object to be examined is proposed in accordance with a second aspect. The adjustment system comprises a predetermined reference object having known visible reference object features, a sensor system, a data evaluation module and an image processor.

The sensor system is configured to capture image data of an image provided by the optical system or, in the case of a stereoscopic system, of a first and second half-image of an object arranged in a field of view to be imaged by the optical system. The sensor system can be in particular a camera system.

The data evaluation module is connected to the sensor system and is configured to receive the captured image data and to determine from the image data position information of at least two visible reference object features of the predetermined reference object arranged in the field of view. The data evaluation module is furthermore configured to determine position data containing a position deviation—determined by means of at least one reference point—of an image—provided by the optical system—of the object to be examined or, in the case of a stereoscopic optical system, of a first and second half-image of the object to be examined by means of the sensor system.

The image processor is connected to the data evaluation module and is configured to ascertain an optical distortion of the image or of the first and/or second half-image from the position information of the at least two visible reference object features of the reference object and to set a corresponding geometric rectification of received image data. Furthermore, the image processor is configured to set a corresponding displacement of received image data of the image or of the first and/or second half-image in a manner corresponding to the position deviation captured.

Advantageously, the adjustment system according to the invention therefore allows an improved adjustment and distortion correction of the image or of the two stereoscopic half-images of an optical system. In this case, the data evaluation module and the image processor can be used both for the static adjustment steps, which are carried out with the reference objet, and for the dynamic adjustment steps, during the operation of the optical apparatus.

Since the adjustment system according to the invention makes hardly any requirements of the stereoscopic optical system, it can be used in a multiplicity of fields of application, in particular stereoscopic fields of application. In this case, the adjustment system requires such a small number of user inputs, such as an activation or deactivation, for example, that it can be used rapidly, safely and in an uncomplicated manner by users of the optical system, that is to say for example medical technical personnel, even without special knowledge in the field of camera adjustment or calibration.

Preferred embodiments of the adjustment system according to the invention in accordance with the second aspect of the invention are mentioned below.

In one preferred embodiment, the data evaluation module for use in a stereoscopic optical system is configured to determine a first vertical and/or horizontal image coordinate of an examination object feature of the object to be examined in the first half-image of the object to be examined and a second corresponding and vertical and/or horizontal image coordinate of the examination object feature in the second half-image of the object to be examined. In this case, a possible horizontal image coordinate is determined with respect to a horizontal image axis which lies in an image plane of the stereoscopic optical system and intersects both optical axes of the stereoscopic optical system. A possible vertical image coordinate is furthermore determined with respect to a vertical image axis which lies in the image plane of the optical system and perpendicularly to the horizontal image axis.

In the context of the invention, the respective vertical or horizontal image coordinates can be determined along the vertical or horizontal image axis, but also along a direction that is oriented substantially along the vertical or horizontal image axis, but does not correspond thereto.

Furthermore, the vertical or horizontal image coordinates can be ascertained as virtual image coordinates directly from an imaging of the object to be examined or from examination object data obtained by processing of the imaging.

In one preferred embodiment, the adjustment system furthermore comprises a storage module, which is connected to the image processor and is configured to store the setting of the geometric rectification and/or the setting of the displacement as adjustment parameter(s). As a result, it is possible to have recourse to the adjustment parameters at a later point in time during use of the adjustment system. In this case, a set of adjustment parameters concerning a concrete setting is also considered as adjustment parameters. Preferably, the setting of the geometric rectification can be stored, as a result of which the determination of the position information is not necessary for every capture of an object to be examined by the optical system. Therefore, a storage module leads to a short adjustment duration of the adjustment system, which is advantageous in particular for moving objects to be examined. In one variant of this embodiment, the storage module is additionally or alternatively used to access the captured position data from earlier points in time and thereby to determine acceleration information. In this case, a position of the at least one reference point is determined at at least two different points in time. This is particularly advantageous for adjusting the image processor given the presence of a regular movement of the optical system and/or of the object to be examined, such as, for example, in the case of wobbling of the optical system.

In a further preferred embodiment, the predetermined reference object is a measurement chart that represents predetermined geometric shapes in a predetermined manner. In other embodiments, the reference object is a printed film, a structured background or a geometric body arranged in a predetermined manner. The predetermined geometric shapes can advantageously be points, rectangles or other polygon progressions. In one particularly advantageous variant, the data evaluation module is configured to initiate performance of the static adjustment step by determination of the position information if at least one predefined reference object feature is detected by the sensor system. As a result, the position information can be determined in an automated manner precisely when the reference object is arranged in the field of view to be imaged, which saves a user input in this regard.

In a further embodiment, the adjustment system furthermore comprises an illumination device configured to provide a light beam that is directed onto the object to be examined. As a result, for the objects to be examined, a visible examination object feature can be provided simply and in a reproducible manner. In one variant of this embodiment, at least two light beams that are directed onto the object to be examined are provided. In a further variant, the illumination device is configured to provide the light beam in a pulsed manner and/or in a spectral range that is imperceptible to users of the optical system. This makes it possible to ensure that capture of the object to be examined is not impaired by the adjustment system according to the invention. In one variant, the light beam forms a structured illumination of the object.

In a further embodiment, an adjustment module of the image processor is configured to set the geometric rectification and also the displacement from received image data. In one variant of this embodiment, the adjustment module is arranged in a housing of the image processor. In another variant, the adjustment module is arranged in a manner spatially separated from a remainder of the image processor, but is electrically connected thereto.

In order to achieve the object mentioned above, a use of an embodiment of the adjustment system in accordance with the second aspect of the invention in a control loop for the dynamic compensation of maladjustments of an optical system, in particular of a stereoscopic optical system, in particular of a stereo endoscope, is proposed in accordance with a third aspect.

The use of the adjustment system according to the invention is particularly advantageous here since it requires few user inputs and can therefore be used largely automatically. By way of example, after an activation of the adjustment system by a user, the control loop can compensate for misadjustments of the optical system in an automated manner.

In one embodiment, the dynamic compensation of misadjustments is configured in such a way that the ascertained settings of the geometric rectification and/or of the corresponding displacement are used by the image processor in such a way that electronic image masks for delimiting an image field to be output are arranged in a manner corresponding to the settings.

Furthermore, in order to achieve the object mentioned above, in accordance with a fourth aspect, a medical apparatus, in particular a medical stereoscopic apparatus, in particular a stereo endoscope, is proposed, which comprises an embodiment of the adjustment system in accordance with the second aspect of the invention.

A medical stereoscopic apparatus in accordance with the fourth aspect of the invention is particularly advantageous since it allows the user, that is to say the medical technical personnel, to perform an adjustment with the adjustment system rapidly, safely and in an uncomplicated manner without special knowledge in the field of camera adjustment or calibration.

In accordance with a fifth aspect of the invention, in order to achieve the object mentioned above, a computer program is proposed which is suitable for controlling an embodiment of the method in accordance with the first aspect of the invention by means of a computer.

The computer program is preferably executed on a processor that forms a part of the image processor. Preferably, the processor is in this case a part of a stereo endoscopy system.

BRIEF DESCRIPTION OF THE DRAWINGS

The invention will now be explained in greater detail on the basis of exemplary embodiments illustrated schematically in the figures. In the figures.

DETAILED DESCRIPTION

Figure 1:
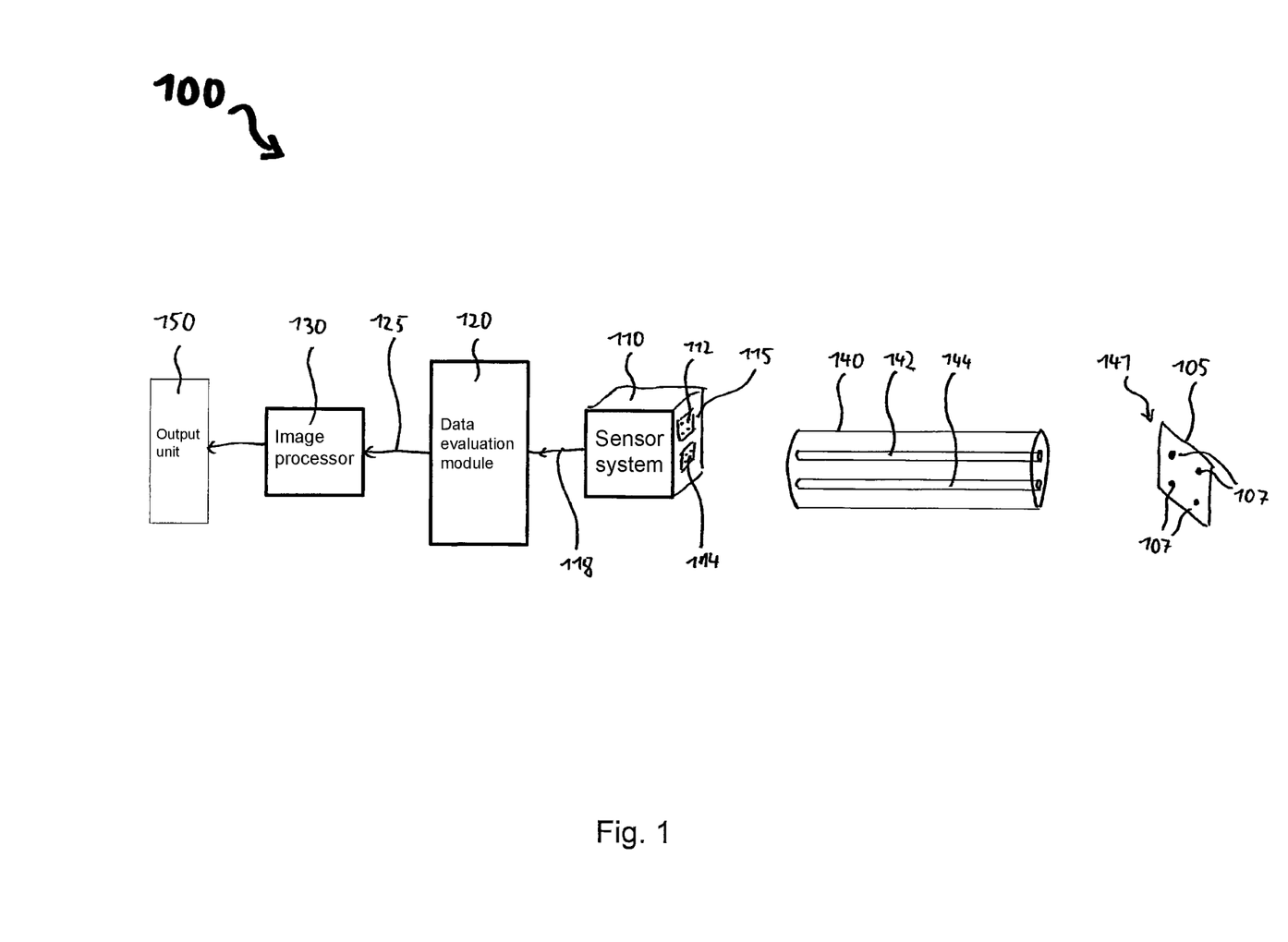
FIG. 1 shows a first exemplary embodiment of an adjustment system in accordance with the second aspect of the invention.

FIG. 1 shows a first exemplary embodiment of an adjustment system 100.

The adjustment system 100 comprises a predetermined reference object 105, a sensor system 110, a data evaluation module 120 and an image processor 130.

The reference object 105 has known visible reference object features 107. In this case, the reference object 105 is arranged such that the reference object features 107, which are configured as points on a measurement chart in the exemplary embodiment shown, can be imaged by a stereoscopic optical system 140.

In the exemplary embodiment illustrated, the stereoscopic optical system 140 is a stereo endoscope having a first 142 and second 144 optical channel, through which a first 112 and second half-image 114 of the reference object 105 can be imaged on an imaging area 115 of the sensor system 110. In exemplary embodiments that are not illustrated, the optical system is configured in a monoscopic fashion.

The sensor system 110 is configured here to capture image data 118 of the first half-image 112 and second half-image 114 imaged on the imaging area 115. In the exemplary embodiment illustrated, the sensor system 110 is a CCD camera system. In other exemplary embodiments, other camera systems, such as CMOS camera systems, for example, are used. Objects are imaged on the imaging area 115 precisely when they are arranged in a field of view 141 of the optical system 140.

The data evaluation module 120 is electrically connected to the sensor system 110 and configured to receive the captured image data 118. For the case illustrated in FIG. 1 where the reference object 105 is arranged in the field of view 141, the data evaluation module 120 is configured to determine from the image data 118 position information 125 of at least two visible reference object features 107 of the predetermined reference object 105 arranged in the field of view 141. For this purpose, image data 118 of the first and second half-images 112, 114 are used by the data evaluation module 120. This described static capture of reference object features 107 typically constitutes first, static adjustment steps of an adjustment to be carried out with the adjustment system. In the second, dynamic adjustment steps illustrated in FIG. 2, image data 118 of the object to be examined are received by the data evaluation module 120. In this case, the data evaluation module 120 is configured to determine a first vertical and/or horizontal image coordinate of an examination object feature of the object to be examined in the first half-image 112 of the object to be examined and a second correspondingly vertical and horizontal image coordinate of the examination object feature in the second half-image 114 of the object to be examined, which is explained in greater detail in the context of FIG. 4. The image coordinates therefore describe position data containing a position deviation of the first and second half-images, said position deviation being determined by means of at least one reference point. In this case, the horizontal image coordinate is determined with respect to a horizontal image axis which lies on the imaging area 115 of the stereoscopic optical system 140 and intersects both optical axes of the first channel 142 and second channel 144 of the stereoscopic optical system 140. The vertical image coordinate is determined with respect to a vertical image axis which lies on the imaging area 115 of the optical system 140 and perpendicularly to the horizontal image axis.

The image processor 130 is electrically connected to the data evaluation module 120. In this case, it is configured to ascertain an optical distortion of the first and second half-images 112, 114 from the position information 125 of the at least two visible reference object features 107 of the reference object 105 and to set a corresponding geometric rectification for the compensation of the optical distortion of received image data. In addition to the optical distortion, in the exemplary embodiment illustrated, a difference in magnification between the first and second half-images 112, 114 is ascertained from the position information 125 and used for setting the geometric rectification.

In the context of the second, dynamic adjustment steps, the image processor 130 is configured to set in a manner corresponding to the position data, that is to say in a manner corresponding to a difference between the first and second vertical image coordinates and between the first and second horizontal image coordinates, a corresponding displacement of received image data of the first and second half-images relative to one another.

The adjustment system 100 according to the invention is therefore configured to set the geometric rectification of future received image data in the context of the first, static adjustment steps via the capture of image data 118 of the reference object 105. Furthermore, the adjustment system 100 is configured to set the corresponding displacement of received image data of the first and second half-images relative to one another by means of subsequent dynamic adjustment steps via the capture of an object to be examined. In this case, the adjustment apparatus is integrated into an image processing of the optical system 140, such that the image processor is connected to an output unit 150 configured as a screen, said output unit providing an optical output on the basis of the received image data. In the exemplary embodiment illustrated, the optical system 140 and the output unit 150 are not part of the adjustment system 100.

In the embodiment illustrated in FIG. 1, the adjustment apparatus can therefore be used for the dynamic compensation of the misadjustments of the stereoscopic optical system 100.

The illustrated use of the adjustment system 100 for a rigid stereo endoscope constitutes one preferred area of use of the invention. Furthermore, however, the adjustment system can also be used for adjustment for other monoscopic and stereoscopic optical systems.

Figure 2:
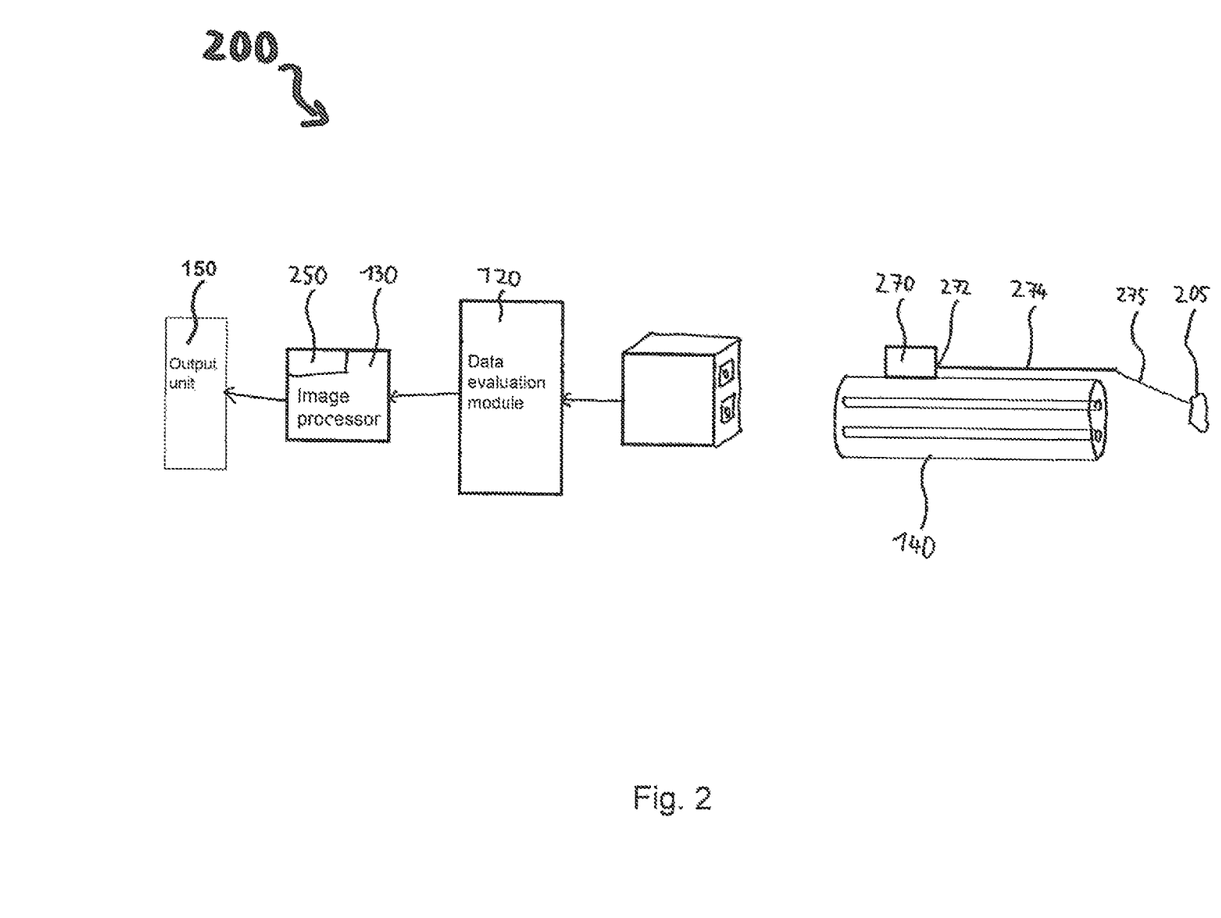
FIG. 2 shows a second exemplary embodiment of the calibration system in accordance with the second aspect of the invention.

FIG. 2 shows a second exemplary embodiment of the adjustment system 200.

In contrast to the adjustment system 100 shown in FIG. 1, the adjustment system 200 comprises a storage module 250, which is electrically connected to the image processor 130. In exemplary embodiments that are not shown, the storage module forms a part of the image processor.

The storage module 250 is configured to store the setting of the geometric rectification and the setting of the displacement as adjustment parameters. In other exemplary embodiments, only the geometric rectification is stored as an adjustment parameter by the storage module, whereas the displacement is always set in an up-to-date manner and is not stored.

A further difference with respect to the adjustment system 100 from FIG. 1 is formed by the illumination device 270, which constitutes a part of the adjustment system 200. The illumination device 270 is configured to provide a light beam 275 that is directed onto the object 205 to be examined. In the present case, the light beam is provided by an LED 272 and a corresponding optical waveguide 274. As a result, the reference point that is to be captured by the data evaluation module 120 is provided particularly simply and advantageously. In one exemplary embodiment, which is not illustrated, the illumination device regularly provides short light pulses such that the user of the optical system 140 is not permanently disturbed by an image of the light beam when viewing the object to be examined. During the duration of the light pulse, in this case, in one variant of the exemplary embodiment that is not illustrated, the image reproduction of the optical system 140 can be interrupted.

Figure 3:
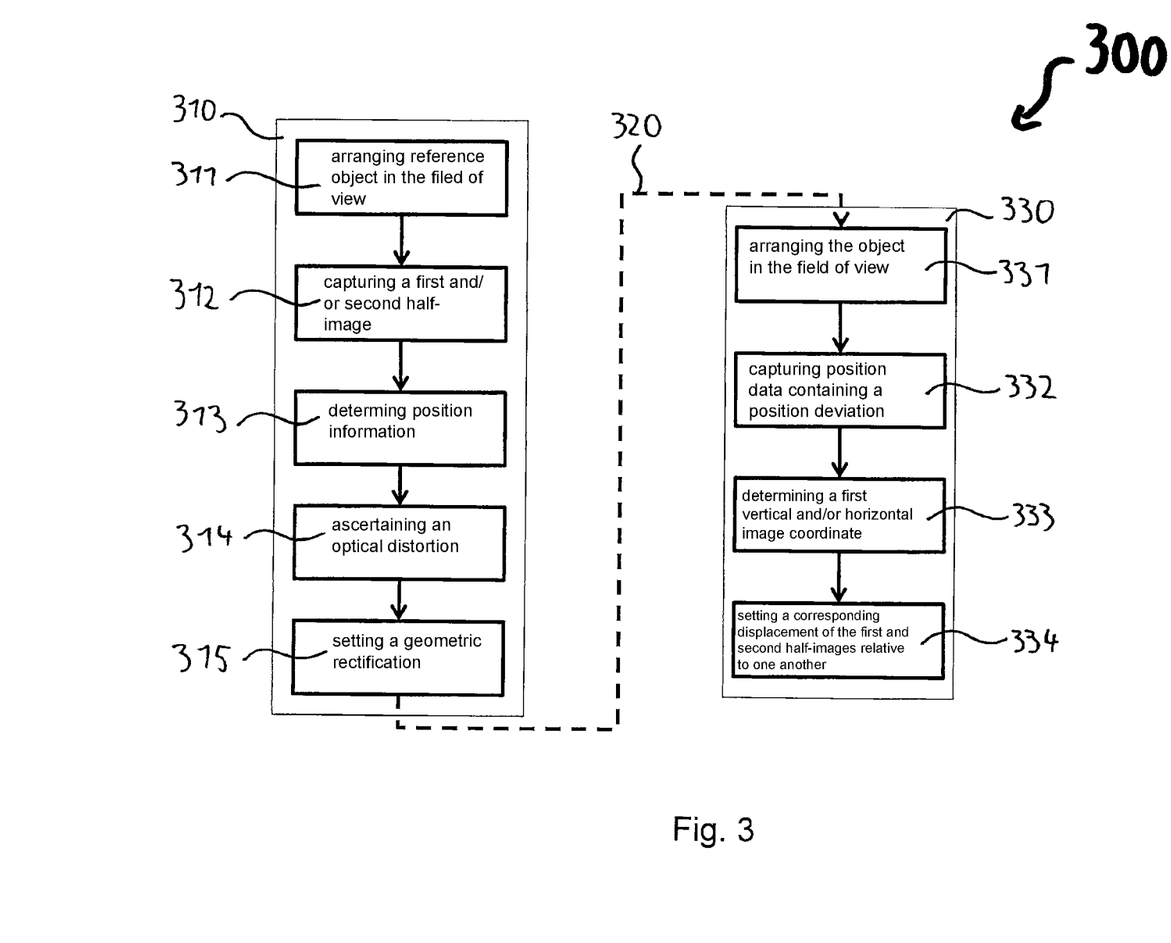
FIG. 3 shows one exemplary embodiment of a method in accordance with the first aspect of the invention.

FIG. 3 shows one exemplary embodiment of a method 300 in accordance with the first aspect of the invention. Said method 300 for adjusting a stereoscopic optical system comprises 5 steps 311, 312, 313, 314, 315, which form the first, static adjustment steps 310, and 4 steps 331, 332, 333, 334, which form the second, dynamic adjustment steps 330. A transition 320 between the last of the first, static adjustment steps 310 and the first of the second, dynamic adjustment steps 330 can extend over a long period of time, but can also be very short. This depends on the length of the period of time required by a user of a system that partly performs the method to observe an object to be examined by means of the stereoscopic optical system after capture of a reference object.

The first, static adjustment steps 310 comprise the steps presented below.

A first step 311 involves arranging a predetermined reference object having known visible reference object features in the field of view to be imaged by the optical system.

A further step 312 involves capturing a first and/or second half-image—provided by the optical system—of the predetermined reference object by means of a sensor system.

A next step 313 involves determining position information of at least two visible reference object features of the predetermined reference object that are imaged in the first and/or second half-image.

Furthermore, a subsequent step 314 involves ascertaining an optical distortion of the first and/or second half-image from the position information of the at least two visible reference object features.

A last step 315 of the first, static adjustment steps 310 involves adjusting an image processor, which is at least indirectly connected to the sensor system, by setting a geometric rectification in a manner corresponding to the optical distortion ascertained.

During operation of the optical system for capturing an object to be examined, the method comprises the steps explained below in the context of the second, dynamic adjustment steps 330.

Firstly, the dynamic adjustment steps 330 comprise, in a first step 331, arranging the object to be examined in the field of view to be imaged by the optical system.

A further step 332 involves capturing position data containing a position deviation—determined by means of at least one reference point—of a first and second half-image of the object to be examined by means of the sensor system.

A subsequent step 333 involves determining a first vertical and/or horizontal image coordinate of the reference point in the first half-image and a second correspondingly vertical and/or horizontal image coordinate of the reference point in the second half-image. In this case, a possible horizontal image coordinate is determined with respect to a horizontal image axis that lies within an image plane of the stereoscopic optical system and intersects both optical axes of the stereoscopic optical system. A possible vertical image coordinate is in turn determined with respect to a vertical image axis that lies within the image plane of the optical system and perpendicularly to the horizontal image axis.

A last step 334 of the method 300 consists of adjusting the image processor in a manner corresponding to the position deviation ascertained, that is to say in a manner corresponding to a difference between the first and second vertical image coordinates and/or between the first and second horizontal image coordinates, by setting a corresponding displacement of the first and second half-images relative to one another by means of the image processor.

In some variants of this exemplary embodiment, the method can also be performed in such a way that the static adjustment steps 310 are performed significantly less frequently than the dynamic adjustment steps 330. In this case, the settings obtained by means of the static adjustment steps 310 are stored as adjustment parameters and used in each case for adjustment after the dynamic adjustment steps 330. The duration of the entire adjustment process can advantageously be reduced as a result. Furthermore, a data transmission rate to the image processor can be kept low, which has an advantageous effect on the technical requirements made of the corresponding adjustment system and the optical system.

Furthermore, the method can also be performed with a monoscopic optical system. In this case, the position deviation is not determined by means of a comparison between the first and second half-images, but rather by means of at least one reference point of an image of the object to be examined, said image being provided by the optical system.

Figure 4:
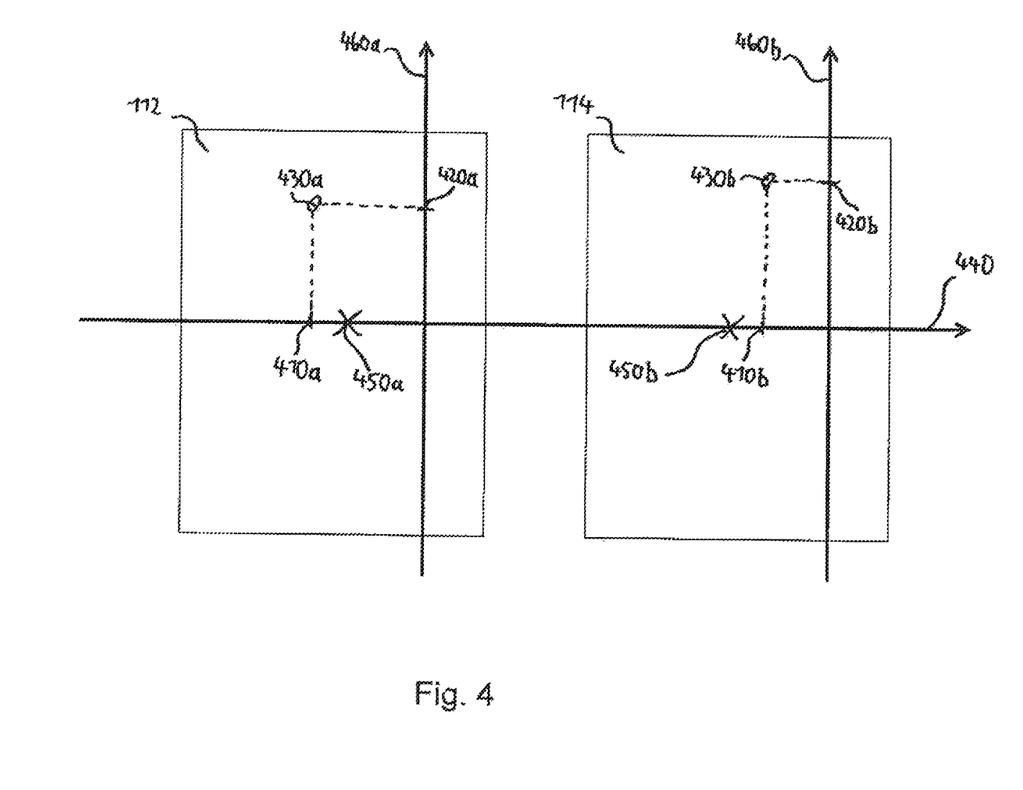
FIG. 4 shows an illustration of a process of determining horizontal and vertical image coordinates in accordance with the exemplary embodiment of the method in accordance with the first aspect of the invention.

FIG. 4 shows an illustration of a process of determining horizontal and vertical image coordinates 410a, 410b, 420a, 420b in accordance with the exemplary embodiment of the method 300.

In this case, a plan view of the imaging area 115 of the sensor system 110 is shown, wherein the first half-image 112 and the second half-image 114 are imaged separately from one another. In this case, the examination object feature 430a, 430b is imaged in the first half-image 112 and second half-image 114 of the stereoscopic optical system.

The horizontal image coordinates 410a, 410b of the examination object feature 430a, 430b in the first and second half-images 112, 114 are determined with respect to a horizontal image axis 440. Said horizontal image axis 440 lies within the image plane of the stereoscopic optical system, said image plane being formed by the imaging area 115, and it intersects both optical axes of the stereoscopic optical system. The intersection points 450a, 450b are represented as crosses.

The vertical image coordinates 420a, 420b of the examination object feature 430a, 430b are determined with respect to a vertical image axis 460a, 460b. The vertical image axis 460a, 460b lies within the image plane of the stereoscopic optical system, said image plane being formed by the imaging area 115, and is perpendicular to the horizontal image axis 440. Since the intersection point of the vertical image axis 460a, 460b with the horizontal image axis 440 is unimportant, FIG. 4 illustrates the vertical image axis 460a, 460b both for the first half-image 112 and for the second half-image 114 for reasons of clarity.

In an exemplary embodiment that is not illustrated, the horizontal image axis is not configured as a connection between the intersection points of the optical axes of the optical system and the imaging area, but rather is oriented with respect to said intersection points in a predetermined manner on the imaging area.

Figure 5A:
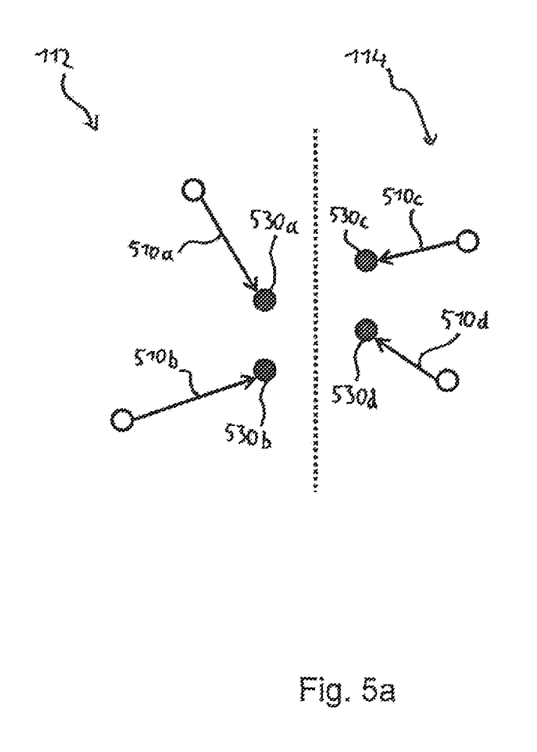
FIGS. 5a, b show an illustration of a process of setting a geometric rectification and a displacement of half-images in accordance with a first variant of the exemplary embodiment of the method in accordance with the first aspect of the invention.
Figure 5B:
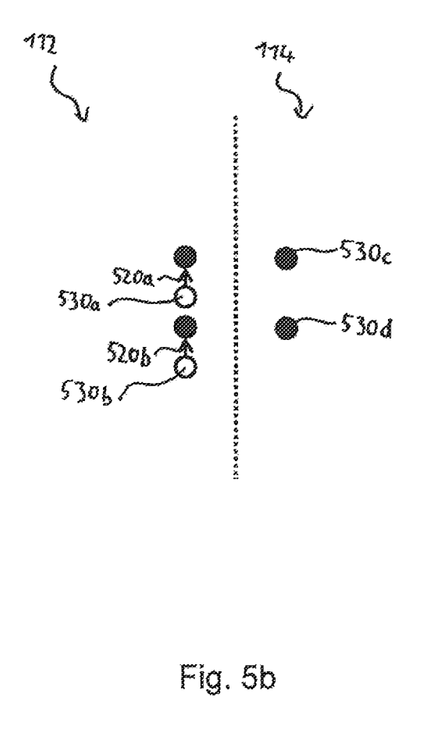

FIGS. 5a, b show an illustration of a process of setting a geometric rectification 510a, 510b, 510c, 510d and a displacement 520a, 520b of half-images 112, 114 in accordance with a first variant of the exemplary embodiment of the method.

In the illustrated variant of the method 300, the corresponding displacement 520a, 520b is set in such a way that image information 530a, 530b, 530c, 530d of the first 112 and/or second half-image 114 that is processed by means of the geometric rectification 510a, 510b, 510c, 510d is displaced in a manner corresponding to the vertical and/or horizontal image coordinates.

In this case, FIG. 5a illustrates the process of the geometric rectification 510a, 510b, 510c, 510d, which proceeds only within the image processor and is therefore invisible to the user in the present variant. FIG. 5b illustrates the subsequent setting of the first half-image 112 by means of a displacement 520a, 520b of the first half-image 112 relative to the second half-image 114. The half-image adjusted in this way can be displayed to the user on a stereo screen. The user can then see an adjusted and undistorted stereo image.

Figure 6A:
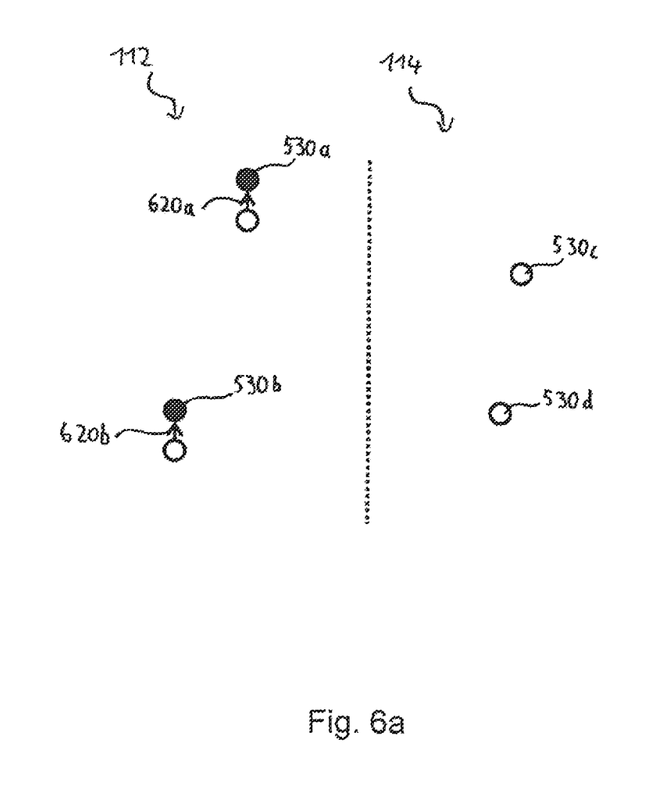
FIGS. 6a, b show an illustration of a process of setting a geometric rectification and a displacement of half-images in accordance with a second variant of the exemplary embodiment of the method in accordance with the first aspect of the invention.
Figure 6B:
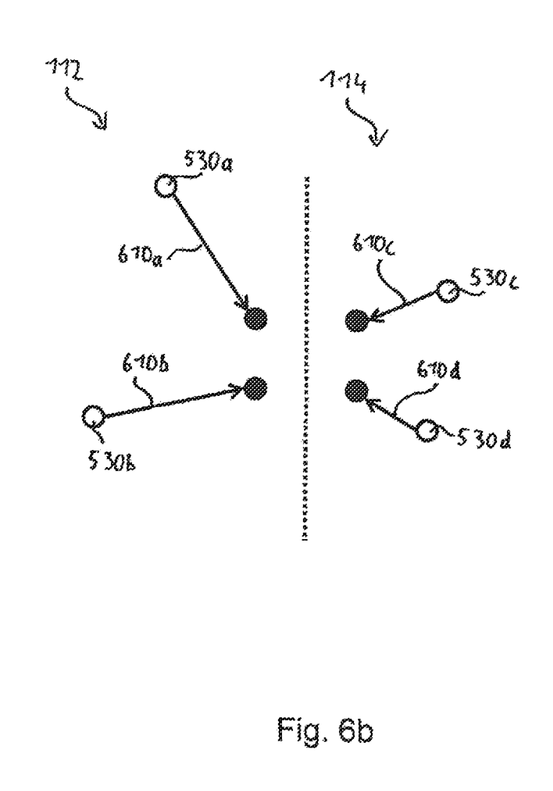

FIGS. 6a, 6b show an illustration of a process of setting the geometric rectification 610a, 610b, 610c, 610d and the displacement 620a, 620b of half-images 112, 114 in accordance with a second variant of the exemplary embodiment of the method.

In the illustrated variant of the method 300, the corresponding displacement 620a, 620b is set in such a way that image information 530a, 530b, 530c, 530d of the first and/or second half-image 112, 114 that is displaced in a manner corresponding to the vertical and/or horizontal image coordinates is processed by means of the geometric rectification 610a, 610b, 610c, 610d.

In this case, FIG. 6a illustrates the process of the displacement 620a, 620b of the first half-image 112 relative to the second half-image 114. FIG. 6b illustrates the subsequent setting of the geometric rectification 610a, 610b, 610c, 610d. Both settings are performed within the image processor and therefore proceed internally. FIGS. 5a, 5b, 6a and 6b therefore serve merely for illustrating possible variants of the method 300. The half-images adjusted in this way can be displayed to the user on a stereo screen in this case. The user then once again sees an adjusted and undistorted stereo image.

In particular, in variants that are not illustrated, image processing steps are performed by the image processor, wherein the adjustment steps illustrated in FIG. 3 are additionally performed in parallel and/or in an offset manner with respect to the image processing steps during operation of the optical system.

LIST OF REFERENCE SIGNS 100, 200 Adjustment system
105 Reference object
107 Reference object features
110 Sensor system
112 First half-image
114 Second half-image
115 Imaging area
118 Image data
120 Data evaluation module
125 Position information
130 Image processor
140 Optical system
141 Field of view
142 First optical channel
144 Second optical channel
150 Output unit
205 Object to be examined
250 Storage module
270 Illumination device
272 LED
274 Optical waveguide
275 Light beam
300 Method
310 Static adjustment steps
311, 312, 313 314, 315 Respective steps of the static adjustment steps
320 Transition of the method
330 Dynamic adjustment steps
331, 332, 333 334 Respective steps of the dynamic adjustment steps
410a, 410b Horizontal image coordinates
420a, 420b Vertical image coordinates
430a, 430b Examination object feature
440 Horizontal image axis
450a, 450b Intersection point
460a, 460b Vertical image axis
510a, 510b, 510c 510d Geometric rectification of the first variant
520a, 520b Displacement of the first variant
530a, 530b, 530c 530d Processed image information
610a, 610b, 610c 610d Geometric rectification of the second variant
620a, 620b Displacement of the second variant

The invention claimed is:

1. A method for adjusting a medical stereoscopic optical system comprising:
arranging a predetermined reference object having known visible reference object features in a field of view captured by the optical system;
capturing a first and a second stereoscopic half-image of the predetermined reference object by means of a sensor system;
determining position information of at least two visible reference object features of the predetermined reference object that are imaged in the first and the second stereoscopic half-images;
ascertaining an optical distortion of the first and the second stereoscopic half-images from the position information of the at least two visible reference object features;
adjusting an image processor, which is at least indirectly connected to the sensor system, by setting a geometric rectification in a manner corresponding to the optical distortion ascertained;
wherein, after said adjusting the image processor the method then comprises repeatedly carrying out the following steps during operation of the optical system for capturing an object to be examined:
arranging the object to be examined in the field of view captured by the optical system;
capturing position data containing a position deviation determined by means of at least one reference point of the first and the second stereoscopic half-images provided by the optical system of the object to be examined relative to each other, wherein said position deviation is a deviation of an image position of said object to be examined with respect to an ideal position of said object in a completely centered optical system; and
adjusting the image processor in a manner corresponding to the captured position deviation between the first and second stereoscopic half-images by setting a corresponding displacement of the first and the second stereoscopic half-images by means of the image processor to perform a correction between the mutual position of the first and second stereoscopic half-images among one another.

2. The method as claimed in claim 1, wherein the object to be examined has at least one visible examination object feature in the field of view captured by the optical system, which serves as a reference point, and/or on the examination object at least one feature on the object that is useable as a reference point is generated by the method, and wherein capturing the position data comprises the following steps:
determining a first vertical and/or horizontal image coordinate of the at least one reference point in the first half-image and a second correspondingly vertical and/or horizontal image coordinate of the at least one reference point in the second half-image,
wherein a possible horizontal image coordinate is determined with respect to a horizontal image axis which lies within an image plane of the stereoscopic optical system and intersects both optical axes of the stereoscopic optical system, and
wherein a possible vertical image coordinate is determined with respect to a vertical image axis which lies within the image plane of the optical system and perpendicularly to the horizontal image axis.

3. The method as claimed in claim 2, wherein the first and second half-images of the predetermined reference object are captured by the sensor system, and wherein adjusting the image processor is carried out by a comparison of the at least two known visible reference object features imaged on the first half-image with the at least two known visible reference object features imaged on the second half-image.

4. The method as claimed in claim 3, wherein the method comprises, besides ascertaining the optical distortion, ascertaining a difference in magnification between the first and second half-images, or a relative displacement between the first and second half-images, or a rotation between the first and second half-images, or a combination thereof.

5. The method as claimed in claim 1, wherein setting the corresponding displacement is carried out in such a way that image information processed by the geometric rectification is displaced in a manner corresponding to the position data.

6. The method as claimed in claim 1, wherein setting the corresponding displacement is carried out in such a way that image information displaced in a manner corresponding to position data is processed by the geometric rectification.

7. The method as claimed in claim 1, wherein furthermore the setting of the geometric rectification and/or the setting of the displacement are/is stored as adjustment parameter(s).

8. The method as claimed in claim 1, wherein the at least one reference point is formed by providing a light beam directed onto the object to be examined.

9. A computer program stored on a non-transitory memory for controlling a method as claimed in claim 1 by means of a computer executing said computer program.

10. An adjustment system for use with a medical stereoscopic optical system for capturing an object to be examined, comprising:
a predetermined reference object having known visible reference object features;
a sensor system configured to capture a first and a second stereoscopic half-image of an object arranged in a field of view to be imaged by the optical system; and
a data evaluation module, which is connected to the sensor system and is configured to receive the image data captured by the sensor system and to determine from the image data position information of at least two visible reference object features of the predetermined reference object arranged in the field of view, and which is furthermore configured to determine position data containing a position deviation of the first and the second stereoscopic half-images of the object to be examined relative to each other; and
an image processor, which is connected to the data evaluation module and is configured to repeatedly ascertain an optical distortion of the first and the second stereoscopic half-images from the position information of the at least two visible reference object features of the reference object and to set a corresponding geometric rectification of received image data, and which is then configured to set a corresponding displacement of received image data of the first and the second stereoscopic half-images in a manner corresponding to the position deviation captured between the first and second stereoscopic half-images to perform a correction between the mutual position of the first and second stereoscopic half-images among one another, wherein said position deviation is a deviation of an image position of said object to be examined with respect to an ideal position of said object in a completely centered optical system.

11. The adjustment system as claimed in claim 10, which furthermore comprises a storage module, which is connected to the image processor and is configured to store the setting of the geometric rectification and/or the setting of the displacement as adjustment parameter(s).

12. The adjustment system as claimed in claim 10, wherein the predetermined reference object is a measurement chart that represents predetermined geometric shapes in a predetermined manner.

13. The adjustment system as claimed in claim 10, which furthermore comprises an illumination device configured to provide a light beam that is directed onto the object to be examined.

14. The use of the adjustment system as claimed in claim 10 in a control loop for the dynamic compensation of misadjustments of an optical system.

15. A medical apparatus, which comprises an adjustment system as claimed in claim 10.

16. The medical apparatus as claimed in claim 15, wherein the medical stereoscopic is a stereo endoscope.

17. The use of the adjustment system as claimed in claim 10, wherein the stereoscopic optical system is a stereo endoscope.

* * * * *